US00PP31643P2

(12) United States Plant Patent
Meilland

(10) Patent No.: US PP31,643 P2
(45) Date of Patent: Apr. 14, 2020

(54) BEDDING ROSE PLANT NAMED 'MEIHAMIGA'

(50) Latin Name: *Rosa hybrida*
Varietal Denomination: MEIHAMIGA

(71) Applicant: THE CONARD-PYLE COMPANY, West Grove, PA (US)

(72) Inventor: Alain Antoine Meilland, Antibes (FR)

(73) Assignee: THE CONARD-PYLE COMPANY, West Grove, PA (US)

( * ) Notice: Subject to any disclaimer, the term of this patent is extended or adjusted under 35 U.S.C. 154(b) by 0 days.

(21) Appl. No.: 16/350,629

(22) Filed: Dec. 12, 2018

(51) Int. Cl.
*A01H 5/02* (2018.01)
*A01H 6/74* (2018.01)

(52) U.S. Cl.
USPC ..... Plt./107
CPC ..... *A01H 6/74* (2018.05)

(58) Field of Classification Search
USPC ..... Plt./107
CPC ..... A01H 5/0222
See application file for complete search history.

(56) References Cited

U.S. PATENT DOCUMENTS

PP9,469 P 3/1996 Meilland et al.

*Primary Examiner* — Kent L Bell
(74) *Attorney, Agent, or Firm* — Buchanan Ingersoll & Rooney PC

(57) ABSTRACT

A new and distinct variety of bedding rose plant, herein referred to by its cultivar name, 'MEIHAMIGA', is provided which forms very abundantly on a nearly continuous basis attractive, cup shaped pink colored flowers. Attractive, glossy, dense foliage is formed, which contrasts beautifully with the blossoms. A ground cover growth habit is displayed. The disease tolerance is very good, particularly against black spot. The new variety is well suited for proving attractive ornamentation in the landscape.

1 Drawing Sheet

Botanical/commercial classification:
Latin name—*Rosa hybrida.*
Common name—Bedding Rose Plant.
Varietal denomination—'MEIHAMIGA'.

SUMMARY OF THE INVENTION

The new variety of *Rosa hybrida* Bedding Rose plant was created by artificial pollination wherein two parents were crossed which previously had been studied in the hope that they would contribute the desired characteristics. The female parent (i.e., the seed parent) was the 'KORIMRO' variety. The male parent (i.e., the pollen parent) was an unnamed seedling which was the product of the cross between the 'KORMAX' variety and an unnamed seedling.

The parentage of the new variety can be summarized as follows:

'KORIMRO' x ('KORMAX' x unnamed seedling)

The seeds resulting from the above pollination were sown and small plants were obtained which were physically and biologically different from each other. Selective study resulted in the identification of a single plant of the new variety.

It was found that the new variety of Bedding Rose plant of the present invention possesses the following combination of characteristics:

(a) forms attractive, cup shaped, pink colored flowers,
(b) provides attractive, dense, glossy foliage,
(c) exhibits a compact ground cover habit,
(d) exhibits very good tolerance to diseases, particularly against black spot, and
(e) is well suited for providing attractive ornamentation.

The new variety well meets the needs of the horticultural industry. It can be grown to advantage as ornamentation in parks, gardens, public areas, and in residential settings. Accordingly, the plant is particularly well suited for growing in the landscape.

The new variety of the present invention can readily be distinguished from its ancestors. More specifically, the 'KORIMRO' variety (i.e., the seed parent) displays light pink colored blossoms and the 'KORMAX' variety (i.e., a parent of the pollen parent) displays red colored blossoms, whereas the new variety displays pink colored blossoms. In addition, the pollen parent ('KORMAX' x unnamed seedling) displays red colored blossoms, whereas the new variety displays pink colored blossoms. Moreover, new variety can be readily distinguished from other related similar non-parental varieties. For example, the 'MEIBONRIB' variety (U.S. Plant Pat. No. 9,469) displays a larger flower compared to the new variety.

The new variety has been found to undergo asexual propagation in France by a number of routes, including budding, grafting, and the use of cuttings. Asexual propagation by the above-mentioned techniques in France has shown that the characteristics of the new variety are stable and are strictly transmissible by such asexual propagation from one generation to another. Accordingly, the new variety undergoes asexual propagation in a true-to-type manner.

The new variety has been named 'MEIHAMIGA'.

BRIEF DESCRIPTION OF THE PHOTOGRAPH

The accompanying photograph of FIG. 1 shows as nearly true as it is reasonably possible to make the same, in a color illustration of this character, typical specimens of the plant parts of the new variety. The rose plants of the new variety were approximately two years of age and were observed during June while budded on their own roots and growing outdoors at Le Cannet des Maures, Var, France. Dimensions in centimeters are indicated at the bottom of FIG. 1.

Element 1—illustrates a specimen of a young shoot.

Element 2—illustrates a specimen of a floral bud before the opening of the sepals.

Element 3—illustrates a specimen of a floral bud at the opening of the sepals.

Element 4—illustrates a specimen of a floral bud at the opening of the petals.

Element 5—illustrates a specimen of a flower in the course of opening.

Element 6—illustrates a specimen of an open flower—plan view—obverse.

Element 7—illustrates a specimen of an open flower—plan view—reverse.

Element 8—illustrates a specimen of a fully open flower—plan view—obverse.

Element 9—illustrates a specimen of a fully open flower—plan view—reverse.

Element 10—illustrates a specimen of a floral receptacle showing arrangement of the stamens and pistils.

Element 11—illustrates a specimen of a floral receptacle showing arrangement of the pistils (stamens removed).

Element 12—illustrates a specimen of a flowering stem.

Element 13—illustrates a specimen of a leaf with 3 leaflets—plan view—upper surface.

Element 14—illustrates a specimen of a leaf with 7 leaflets—plan view—upper surface.

Element 15—illustrates a specimen of a leaf with 7 leaflets—plan view—under surface.

Element 16—illustrates a specimen of buds in cluster.

DETAILED BOTANICAL DESCRIPTION

The chart used in the identification of the colors is that of The Royal Horticultural Society (R.H.S. Colour Chart, 2001 edition), London, England. The terminology which precedes reference to the chart has been added to indicate the corresponding color in more common terms. The description is based on the observation of two-year-old specimens of the new variety during June while budded on their own roots and growing outdoors at Le Cannet des Maures, Var, France.

Class: Bedding Rose Plant.

Plant:

*Habit*.—Ground cover.

*Height*.—Approximately 60 cm on average.

*Width*.—Approximately 150 cm on average.

Branches:

*Color*.—Young stems: commonly near Yellow-Green Group 146C. Adult wood: commonly near Yellow-Green Group 146B.

*Length*.—Typically 40 cm to 100 cm on average.

*Diameter*.—Typically 0.4 cm to 1.0 cm on average.

*Internode length*.—Typically 4.0 cm to 8.0 cm on average.

*Thorns*.—Configuration on adult stems: upright on the upper surface and slightly concave on the under surface. Long prickles (≥0.5 cm) — quantity: commonly approximately 14 thorns per 10 cm long young stem and commonly 9 thorns per 10 cm long adult stem. Long prickles (≥0.5 cm) — base shape: oval. Long prickles (≥0.5 cm) — size: commonly near 0.6 cm in length on average on young stems and commonly near 0.9 cm on average on adult stems. Long prickles (≥0.5 cm) — color: commonly near Greyed-Orange Group 164B on young stems and commonly near Greyed-Orange Group 166B on adult stems. Small prickles (<0.5 cm) — quantity: none observed.

Foliage:

*General appearance*.—Dense with a glossy aspect.

*Number of leaflets*.—3, 5, and 7; most often 7.

*Terminal leaflet*.—Length: approximately 2.5 cm on average. Width: approximately 2.0 cm on average.

*New foliage*.—Upper surface color: commonly near Green Group 137A. Under surface color: commonly near Green Group 138B.

*Adult foliage*.—Upper surface color: commonly near Green Group 137A. Under surface color: commonly near Green Group 137C.

*Entire leaf*.—Length: typically 6.5 cm to 11.5 cm on average. Width: typically 4.0 cm to 6.0 cm on average.

Leaflets:

*Shape*.—Tip: pointed. Base: obtuse.

*Texture*.—Leathery.

*General appearance*.—Oval.

*Edge*.—Slightly denticulate.

*Serration*.—Small and single.

*Petiole rachis*.—Color of upper surface: commonly near Green Group 137A. Color of under surface: commonly near Yellow-Green Group 146C. Length: typically 3.0 cm to 5.0 cm on average. Width: typically 0.1 cm on average.

*Petioles*.—Upper surface: no glandular. Under surface: few prickles. Color of upper surface: commonly near Green Group 137A. Color of under surface: commonly near Yellow-Green Group 146C. Diameter: typically near 0.1 cm on average. Petiole length of terminal leaflet: commonly near 0.7 cm on average.

*Stipules*.—General appearance: adnate, pectinate and rather broad. Length: approximately 1.2 cm on average. Width: approximately 0.4 cm on average. Color of upper surface: commonly near Yellow-Green Group 148C. Color of under surface: commonly near Yellow-Green Group 146B.

Inflorescence:

*Number of flowers per stem*.—Generally between 3 to 12 flowers per stem.

*Bud*.—Shape: conical. Size: small. Length: approximately 0.6 cm on average. Width: approximately 0.4 cm on average. Color as calyx breaks: upper surface: commonly between near Red-Purple Group 68A and Red-Purple Group 68B. under surface: commonly near Red-Purple Group 68A.

*Sepals*.—Length: approximately 0.7 cm on average. Width: approximately near 0.3 cm on average. Shape: without extensions at the top: elongated, at the base: upright. Margin: hairy. Upper surface: texture: tomentous. color: commonly near Yellow-Green Group 148C. Under surface: texture: smooth. color: commonly near Yellow-Green Group 148B.

*Receptacle*.—Color: commonly near Yellow-Green Group 148B. Length: approximately 0.3 cm on average. Width: approximately 0.3 cm on average. Surface: smooth. Shape: pitcher shaped.

*Peduncle*.—Length: commonly near 2.0 cm on average. Width: approximately 0.1 cm on average. Surface: smooth. Color: commonly near Yellow-Green Group 146B.

*Flower*.—Average diameter when fully open: approximately 4.0 cm on average. Depth: approximately 2.0 cm on average. Borne: commonly between 3 to 12 flowers per stem. Shape: cup shaped. Number of petals under normal conditions: approximately 12 to 14 petals on average. Shape of the petal: cordiform. base: obtuse. top: rounded. Petal margin: entire. Texture of the petal: leathery. Petal length: approximately 1.1 cm on average. Petal width: approximately 1.0 cm on average. Petal arrangement: imbricated without petaloids. Petal drop: petals drop off cleanly before drying. Fragrance: none. Color when opening: very little spot at the base: upper surface and under surface is commonly near Yellow Group 2D. upper surface of the flower: commonly near Red-Purple Group 68B. under surface of the flower: commonly near Red-Purple Group 68A. Color of the open flower: very little spot at the base: upper surface and under surface is commonly near Yellow Group 2D. upper surface of the flower: commonly near Red-Purple Group 68C. under surface of the flower: commonly near Red-Purple Group 68B. Anthers: number is approximately 78 on average, length is approximately 0.1 cm on average, coloration is commonly near Orange Group 28C, and arrangement is regular around styles. Filaments: length is approximately 0.2 cm on average and coloration is commonly near Yellow Group 2C. Styles: length is approximately 0.2 cm on average, coloration is commonly near Yellow-Green Group 150C, and number is approximately 23 on average. Stigmas: size is approximately 0.3 cm on average and coloration is commonly near Yellow-Green Group 150C. Pollen: not available at this stage. Hips: not available at this stage.

Development:

*Vegetation*.—Very strong.

*Lastingness of bloom*.—Approximately 1 week on average.

*Blooming*.—Early in the season, very abundant and nearly continuous, typically blooms May to October.

*USDA hardiness zone*.—Zone 5.

*Tolerance to disease*.—Very good, and particularly against black spot (*Diplocarpon rosae*).

The new 'MEIHAMIGA' variety has not been observed under all possible environmental conditions to date. Accordingly, it is possible that the phenotypic expression may vary somewhat with changes in light intensity and duration, cultural practices, and other environmental conditions.

I claim:

1. A new and distinct variety of Bedding Rose plant characterized by the following combination of characteristics:

a) forms attractive, cup shaped, pink colored flowers, (b) provides attractive, dense, glossy foliage, (c) exhibits a compact ground cover habit, (d) exhibits very good tolerance to diseases, particularly against black spot, and (e) is well suited for providing attractive ornamentation; substantially as herein shown and described.

* * * * *

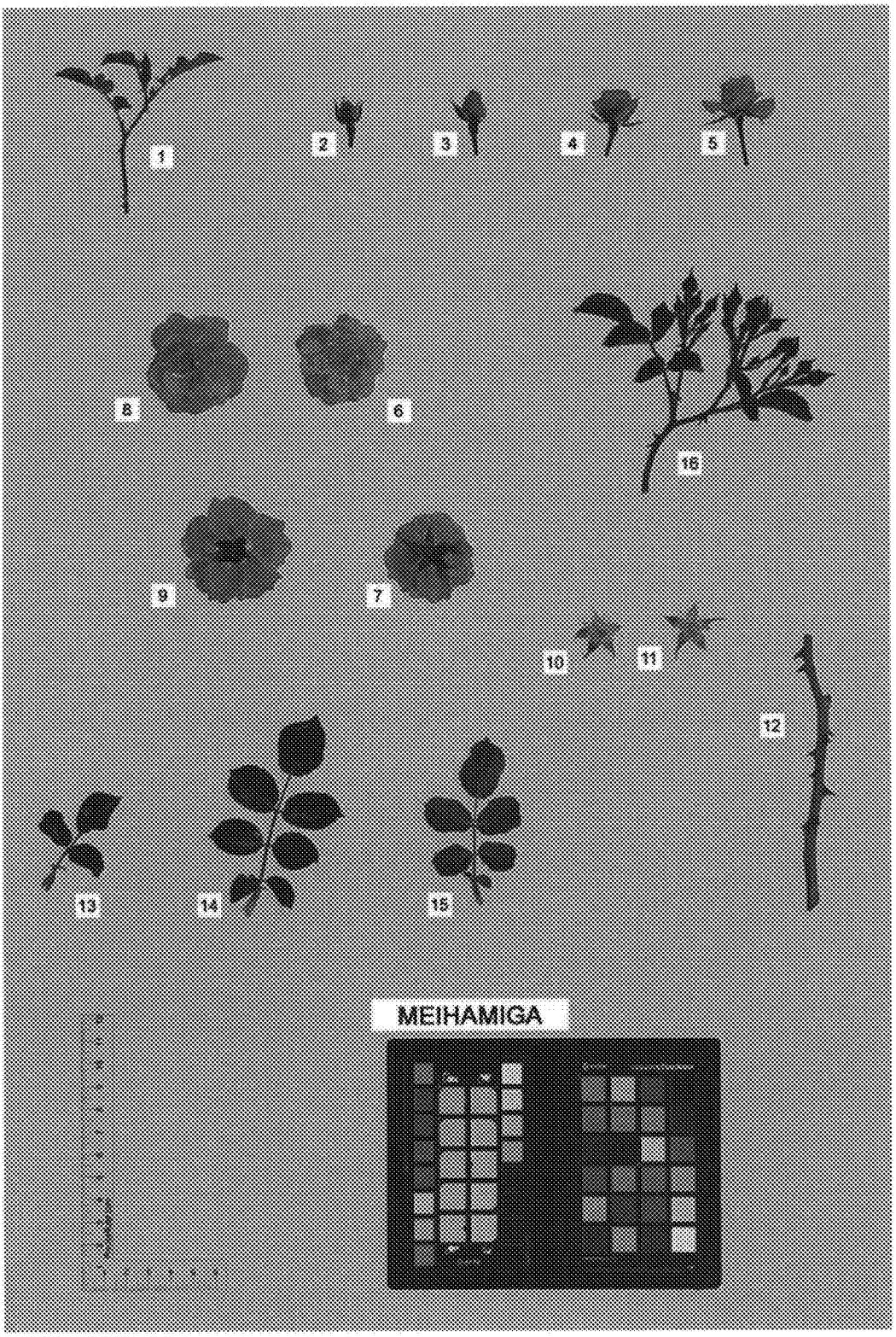
1
2
3
4
5
8
6
16
9
7
10
11
12
13
14
15
MEIHAMIGA